(12) United States Patent
Burneikis

(10) Patent No.: US 7,160,245 B2
(45) Date of Patent: Jan. 9, 2007

(54) METHOD AND DEVICE FOR UMBILICUS PROTECTION DURING ABDOMINAL SURGERY

(76) Inventor: Virginijus Burneikis, 11457 W. Wolf Tooth Pass, Littleton, CO (US) 80127

( * ) Notice: Subject to any disclaimer, the term of this patent is extended or adjusted under 35 U.S.C. 154(b) by 347 days.

(21) Appl. No.: 10/715,097

(22) Filed: Nov. 17, 2003

(65) Prior Publication Data

US 2005/0107804 A1    May 19, 2005

(51) Int. Cl.
A61F 2/00 (2006.01)
A61F 13/00 (2006.01)

(52) U.S. Cl. ............................................. 600/37; 606/1
(58) Field of Classification Search ................ 606/120, 606/139, 232, 148, 1, 151, 184, 72; 600/37
See application file for complete search history.

(56) References Cited

U.S. PATENT DOCUMENTS

| | | | |
|---|---|---|---|
| 2,973,761 A * | 3/1961 | Kohl | 606/140 |
| 5,242,456 A | 9/1993 | Nash et al. | |
| 5,378,628 A | 1/1995 | Grätzel et al. | |
| 5,383,477 A | 1/1995 | DeMatteis | |
| 5,562,684 A | 10/1996 | Kammerer | |
| 5,655,544 A | 8/1997 | Johnson | |
| 6,051,013 A | 4/2000 | Mollenauer | |
| 6,203,554 B1 | 3/2001 | Roberts | |
| 6,454,783 B1 | 9/2002 | Piskun | |

OTHER PUBLICATIONS

Schoeller, Thomas M.D.; Wechselberger, Gottfried M.D.; Otto, Angela M.D.; Rainer, Christian M.D.; Schwabegger, Anton M.D.; Lille, Sean M.D.; Ninkovic, Milomir M.D. "New Technique for Scarless Umbilical Reinsertion in Abdominoplasty Procedures." © 1998American Society of Plastic Surgeons vol. 102(5), Oct. 1998, pp. 1720-1723 Innsbruck, Austria.*

* cited by examiner

Primary Examiner—(Jackie) Tan-Uyen Ho
Assistant Examiner—Natalie Pous
(74) Attorney, Agent, or Firm—Lee G. Meyer, Esq.; Meyer & Associates, LLC

(57) ABSTRACT

A device and method for umbilicus protection during abdominal surgery; and, especially plastic reconstructive and aesthetic surgery requiring umbilicoplasty and/or umbilicus transposition is provided. The device embodies an umbilicus shield, which envelops the umbilical pedicle during abdominal surgery. The device can include a tubular element, having a distal end and a proximal end, containing near its proximal end, means for releasabley retaining suture material from tacking stitches taken in the umbilicus to provide means for drawing the umbilical pedicle into the tubular element. The suture material is advantageously drawn through the tubular element by means of a suture shuttle which contains, proximate its distal end, means for releasabley retaining the suture material. The device facilitates umbilicoplasty and umbilicus transposition during abdominal surgery; prevents nicks or cuts during circum umbilicus dissection; prevents nicks, cuts, or amputation of the umbilicus during defattening; and, reduces the possibility of umbilical pedicle strangulation during rectus abdominis musculoaponeurotic plication. The method prevents such strangulation and assures proper positioning of the orifice and umbilicus during umbilicus transpositions.

16 Claims, 5 Drawing Sheets

METHOD AND DEVICE FOR UMBILICUS PROTECTION DURING ABDOMINAL SURGERY

BACKGROUND OF THE INVENTION

1. Field of the Invention

The present invention relates generally to a method and device for use in abdominal surgery; and, more particularly, to a method and device for protecting the umbilicus during abdominal subcutaneous surgery.

2. Description of Related Art

In recent years elective cosmetic surgery has become more prevalent. With the constant pressure on society to look and act younger, plastic surgeons and dermatologists have derived many youth enhancing medical procedures. For example, removing wrinkles, breast augmentation, liposuction to remove excessive fat, and the like has come into accepted vogue. Although these procedures are usually relatively risk free, complications can cause sever medical problems and even, in some cases, death. Among these complications are infections, skin loss, blood loss, strangulation of circulation, and the like.

Some of these elective procedures are relatively simple and require little patient preparation and are relatively risk free. Examples are Botox® injections, skin peels, certain laser procedures, and the like. These procedures are usually preformed in the physician's office or a clinic, on an outpatient basis; and, are accompanied by minor discomfort and pain. Other elective procedures, however, involve major invasive surgery, requiring general anesthesia, hospitalization, and a rather extended recovery period. Face-lifts, some extensive liposuction, and breast augmentation are among those procedures. Procedures such as these and some others involve extensive subcutaneous invasion, blood loss, extended operating room time, pain management, and an extensive recovery period.

Recently even more radical procedures have been introduced to affect cosmetic appearance. Women, especially after childbirth, develop abdominal disfigurement, such as stretch marks, excessive skin sagging, and the like. In addition, the abdomen, which contains substantial fat cells, tends to enlarge with weight gain disproportionately to the remainder of the anatomy in both men and women. Further, with dramatic weight loss, the abdomen skin cannot return to its former "stretched" configuration, resulting in skin folds or sagging at the lower abdomen. In order to deal with this problem, a procedure known as abdominoplasty, commonly referred to as a "tummy tuck," has been developed.

Abdominoplasty involves the removal of excess skin and fat from the middle and lower abdomen as well as tightening of the abdominal (rectus) muscles. More specifically, this operation is done to tighten the loose skin of the abdomen and repair the weak muscles of the abdominal wall. The procedure is sometimes combined with liposuction to, for example, remove fat, smooth the edges, and improve the contour. If the patient suffers from obesity the panniculus of fat is removed at the same time.

Although abdominoplasty varies, and can even be accomplished, in some cases, by endoscopic methods, the basic procedure for a, so-called, "complete abdominoplasty" is the same. First, a lower abdomen incision is made. The abdominal flap is then lifted and the underlying fat is removed to the abdominal fascia. The abdominal wall muscles are tightened by suturing, the flap is stretched with the excess being removed, and then sutured, preferably below the panty line. The procedure can be "complete" or "partial (mini)." A partial abdominoplasty may take as little as an hour or two, while the complete abdominoplasty takes between two to five hours, depending on the extent of work required.

In a partial abdominoplasty, a short incision is made, and the removal of the umbilicus (umbiliplasty) is usually not required. The skin is then separated only between the incision line and the umbilicus. This abdominal flap is stretched down, while any excess skin is removed. Finally, the abdominal flap is then stitched back into place. In partial abdominoplasty significant strides have been made in surgical procedure using endoscopic assisted methods. One such procedure is disclosed in U.S. Pat. No. 5,655,544 issued in August 1997 to G. W. Johnson. In accordance with this method, the use of abdominal incisions is minimized leaving substantially no visible scars on the abdomen of the patient.

The endoscope assisted abdominoplasty uses two small hidden incisions, one in the umbilicus or on the abdomen or in pre-existing scars or other areas (such as under the armpit) for introduction of the surgical instruments, and a small incision within the pubic hair line for endoscopic and/or direct observation and control of the procedure. While observing the procedure through the endoscope, the surgical instruments are inserted through the umbilical incision to remove fat by liposuction and plicate and repair the muscles by use of a tenaculum and fascial sutures. After removal of the instruments, the small incisions are sutured, and the skin layer allowed to retract and tighten.

While these procedures have met with a modicum of success, they do not lend themselves to a "complete" abdominoplasty. This is primarily due to the fact that a complete abdominoplasty usually requires an umbilicoplasty (repositioning of the umbilicus (belly button)). The complete procedure involves making a long incision from one hipbone to the other above the pubic area. A second incision is made to free the navel from surrounding tissue (circum umbilical pedicle dissection). Next, the skin and subcutaneous fat (abdominal flap) are separated from the abdominal wall to reveal the vertical abdominal muscles (rectus) for tightening. This tightening provides a firmer abdominal wall and helps to narrow the waistline. The abdominal flap is then stretched down and extra skin is removed. A new orifice (belly button hole) is cut for the umbilicus, which is then stitched into place. Finally, the incisions are stitched, dressings are applied, and any excess fluids are drained from the surgical site.

Full or complete abdominoplasty, although an invasive procedure, is routinely performed in hospitals and clinics through out the world. Even though, this procedure has become more or less routine it is fraught with a number of potential complications. Some of the more serious complications relate to the umbilicus (belly button). The umbilicus and umbilical pedicle, to which the umbilical cord was originally attached, is connected to the abdominal fascia tissue and muscle and cannot be repositioned when the epidermis (skin) is repositioned. In order to remove the abdominal flap, remove underlying fatty tissue, and stretch the remaining tissue over the abdomen to remove excess skin, the orifice (belly button opening) must be repositioned to accommodate the umbilical pedicle, which does not move. Thus, when the abdominal flap is stretched and repositioned, a new opening in the abdominal flap is required to access the umbilicus.

In order to accomplish this during complete abdominoplasty, the umbilicus must be cut from the surrounding skin by performing a circum umbilical pedicle dissection. Then, scissors are used to dissect the umbilical stalk from the surrounding fat and tissue down to the muscle fascia. The possibility for nicking or cutting the umbilical stalk during this procedure is substantial.

Then an incision is made along the lower abdomen to facilitate lifting the abdominal flap from the abdomen to "defatten" the abdomen. This dissection is accomplished using, for example, a scalpel and/or electrocautery blade. The possibility for nicking, cutting, or even amputation of the umbilical pedicle during this procedure is substantial. Next, suturing on the midline (rectus abdominis musculoaponeurotic plication) tightens the abdominal fascia muscle. Umbilical pedicle strangulation can occur during this suturing of the abdominal muscles. The separated abdominal flap is then stretched over the defattened abdomen and the access skin trimmed. A new belly button orifice is then cut into the skin after it is stretched and trimmed. Reinserting the umbilicus in the new orifice can also lead to complications such as strangulation, caused by twisting the umbilical pedicle. Sutures are then placed at the incision line to hold the umbilicus, as well as the stretched abdominal flap over the defattened abdomen.

Thus, the complete procedure is somewhat risky using this prior art technique. First, the umbilical pedicle can be cut or nicked during circum umbilical stalk dissection. Thus, there is possible blood supply damage to the umbilicus. Further, since defattening is accomplished under the skin, using a surgical blade, too much tissue may be removed while performing undermining of the flap resulting in nicking, cutting, or amputating the umbilical pedicle. Additionally, once the umbilical pedicle is released from the skin hooks (as described below); it must be re-determined prior to cutting a new orifice. It is difficult to determine the correct umbilicus location under the subcutaneous fat layer for new umbilicus positioning during umbilicus transposition (cutting a new belly button hole and palpating the umbilicus through the skin opening). Twisting of the umbilical pedicle can occur during umbilicus transposition (placement into a new opening in abdomen skin) resulting in strangulation.

Therefore, it would be advantageous to have a device and method for facilitating umbilicus positioning during abdominal surgery and especially plastic reconstructive and aesthetic surgery requiring umbilicoplasty and umbilical stalk transposition. It would be further advantageous to have a device, which prevents nicks, or cuts of the umbilicus during defattening, and assuring proper positioning of the opening during umbilicoplasty and umbilical stalk transposition as well as elimination of umbilical stalk strangulation.

SUMMARY OF THE INVENTION

In accordance with the invention, there is provided a device and method for umbilicus protection during abdominal surgery; and, especially plastic reconstructive and aesthetic surgery requiring umbilicoplasty and/or umbilicus transposition. The device facilitates umbilicoplasty and umbilicus transposition during abdominal surgery; prevents nicks or cuts during circum umbilical pedicle dissection; prevents nicks, cuts, or amputation of the umbilicus during defattening; and, reduces the possibility of umbilical pedicle strangulation during rectus abdominis musculoaponeurotic plication. Likewise, the method prevents such strangulation and assures proper positioning of the orifice and umbilicus during umbilicus transpositions.

A device for protecting the umbilicus during abdominal surgery is an umbilical pedicle shield comprising an open-ended vessel having a proximal and a distal end, which envelops the umbilical pedicle during abdominal surgery. The umbilical pedicle is advantageously drawn into the vessel by means of suture material fastened to the umbilicus by for example a tacking suture. Advantageously this vessel comprises a tubular element, having a distal end and a proximal end. The tubular element contains, near its proximal end, means for releasabley retaining suture material from tacking stitches taken in the umbilicus to provide means for drawing the umbilical pedicle into the tubular element. Advantageously the suture material is drawn through the tubular element by means of a suture shuttle. The suture shuttle element contains, proximate its distal end, means for releasabley retaining the suture material. Advantageously, the means for releasabley retaining the sutures material comprises notched portions in the specified ends of the tubular element and the suture shuttle element.

In accordance with one embodiment, the notched portions of the tubular element are retained on opposing ears disposed peripherally of the proximal end of tubular element, such that the ears can be used to manipulate the tubular element during surgery. In accordance with another aspect the tubular member has a circular lip disposed upon the proximal end and an upstanding collar portion. The circular lip and the collar contain aligned, opposing notches to retain the suture material. In accordance with one aspect, the tubular element contains, on the proximal outer surface thereof, markings in relationship to the notched portions to orient the tubular element, relative to the sutures. Advantageously, these markings are black printed "UP" and "DOWN", R (right) and L (left) wherein each is disposed in each quadrant of the tubular element, wherein UP marks the superior (upper) aspect of the midline on the patient; and, DOWN marks the inferior (bottom) aspect of the midline of the patient.

In accordance with another aspect of the instant invention, the distal end of the tubular element contains a Teflon® coated, electrocautery, cutting, ring-shaped blade to advantageously provide an electrocautery dissector for umbilical pedicle dissection down to the abdominal fascia. In operation, the tubular element so equipped is pushed straight down while simultaneously pulling the suture material taught. In accordance with this aspect, the electrical wires from the electrocautery blade to the energy source are isolated inside the tubular element to insulate it from the patient. Upon completion of umbilical pedicle dissection, the connectors to the energy source are disengaged.

A method for protecting the umbilicus during abdominal surgery wherein umbilicoplasty is indicated is provided. In accordance with this method, the umbilicus is first circum dissected and then drawn into a protective casing or shield. Advantageously, the method comprises the following steps. The umbilicus is first circum dissected; at least a pair of tacking sutures is secured to superior and inferior point of the midline of the umbilicus; the suture shuttle is inserted through the tubular element; the suture material from the tacking sutures is attached to the notches in the distal end of the suture shuttle element; the suture shuttle element is pulled through the tubular element while pushing the tubular element into the circum dissected incision to capture the umbilicus interior the tubular element; the suture material is then tensioned to draw the umbilical pedicle within the tubular element and then attached to the tubular element such that the superior tacking suture corresponds to the "UP" position on the tubular element and the inferior tacking suture corresponds to the "DOWN" position on the tubular element. The pedicle can then be dissected to the abdominal fascia by cutting around the periphery of the tubular element.

In accordance with another aspect, the placed tubular element protects the umbilical pedicle from possible blood supply damage or amputation during the abdominal flap undermining around the umbilical pedicle. In accordance with another aspect, the placed tubular element prevents umbilical pedicle strangulation by suturing during rectus abdominis musculoaponeurotic placation. In accordance with another aspect, the placed tubular element facilitates determination of correct umbilicus location under the abdominal flap during umbilicoplasty (palpating the tubular element including the opening). In accordance with another aspect the placed tubular element having peripheral markings "UP," "DOWN," "L," and "R" markings on the tubular element prevents the umbilical pedicle from twisting during new umbilicus positioning and suturing and as result from strangulation and necrosis.

A method for circum-umbilical dissection and proper positioning of the orifice during umbilicoplasty and umbilicus transposition during abdominal surgery includes the steps of; subcutaneous suturing, at least at a superior and inferior point of the midline of the umbilicus; securing the suture material to the distal end of the suture shuttle; pulling the suture material through the tubular element; and, securing the suture material to the proximal end of tubular element under suitable pressure to at least partially move the pedicle interior the tubular element and tension the distal end of the tubular element against the patient.

In one aspect, the tubular element is used to provide a cutting dye during complete circum umbilical dissection to the abdominal fascia. In another aspect, the tubular element is used to provide protection for the umbilical pedicle during abdominal flap dissection. In accordance with this aspect, the distal end of the tubular element is placed into the complete circum umbilical dissection to rest on the abdominal fascia, while the sutures are tensioned to draw substantially the entire pedicle interior the tubular element. In accordance with another aspect, the tubular element is used to prevent strangulation of the pedicle during rectus abdominis musculoaponeurotic plication. In accordance with this embodiment, the distal end of the tubular element is maintained in tensioned contact with the abdominal fascia, surrounding the umbilicus, during suturing of the abdominal muscle wall. The outer surface of the tubular element prevents the sutured muscle wall from strangling the umbilical pedicle.

In accordance with another aspect, the proximal end of the tubular element is used to facilitate umbilicus transposition. In accordance with this aspect, the abdominal flap is pulled over the proximal end of the tubular element located beneath the abdominal flap. The skin is then dissected about the proximal end of the tubular element to provide the new orifice. In accordance with another aspect, the markings on the tubular element are positioned to prevent strangulation (twisting) of the umbilical pedicle during reattachment of the umbilicus to the abdominal flap.

BRIEF DESCRIPTION OF THE FIGURES

The objects, features, and advantages of the present invention will be apparent to one skilled in the art, in view of the following detailed description in which.

DISCUSSION OF THE SYSTEM NOMENCLATURE

As used herein, the following terms will have the meanings hereinafter set forth. Umbilical means the place on the central abdomen where a narrow cord of tissue connected the developing embryo, or fetus, with the placenta for maternal nourishment. Umbilicoplasty means a circum-umbilical pedicle dissection and transpositioning. Rectus muscle means the muscles forming the abdominal wall. Circum-umbilical pedicle dissection means a circum umbilical incision followed by a dissection of the umbilical pedicle from the surrounding tissue down to the abdomen fascia. Rectus abdominis musculoaponeurotic plication means tightening of the rectus abdominis muscle by suturing along the midline. Abdominal flap means the abdominal skin and under lying subcutaneous fat. Abdominal flap dissection means undermining the skin and subcutaneous fat.

DETAILED DESCRIPTION OF THE INVENTION

The instant invention provides a method and device for umbilicus protection during abdominal surgery and particularly a surgical procedure where safe complete circum umbilical dissection of the umbilical pedicle down to abdominal fascia needs to be performed. Their use, however, is not intended to be limited to these types of surgery alone. Any abdominal surgery wherein the umbilicus site is invaded is intended to be covered by the instant invention. The method and device of the instant invention are particularly advantageous in protecting the umbilicus during abdominal subcutaneous surgery; however, they are particularly useful in plastic reconstructive and aesthetic surgery wherein umbilicoplasty is performed as part of an abdominoplasty procedure. It will be realized by the skilled artisan that the following description is exemplary in nature and embodies advantageous ways of practicing the claimed invention but is not exhaustive of the devices, which are available. As long as the umbilical pedicle is encased or enveloped within the protection or shielding device, the advantages of the broad invention are realized. For example, the encasing element need not be tubular and there need not be a shuttle component; however, these embodiments facilitate the practice of the invention.

Figure 1:
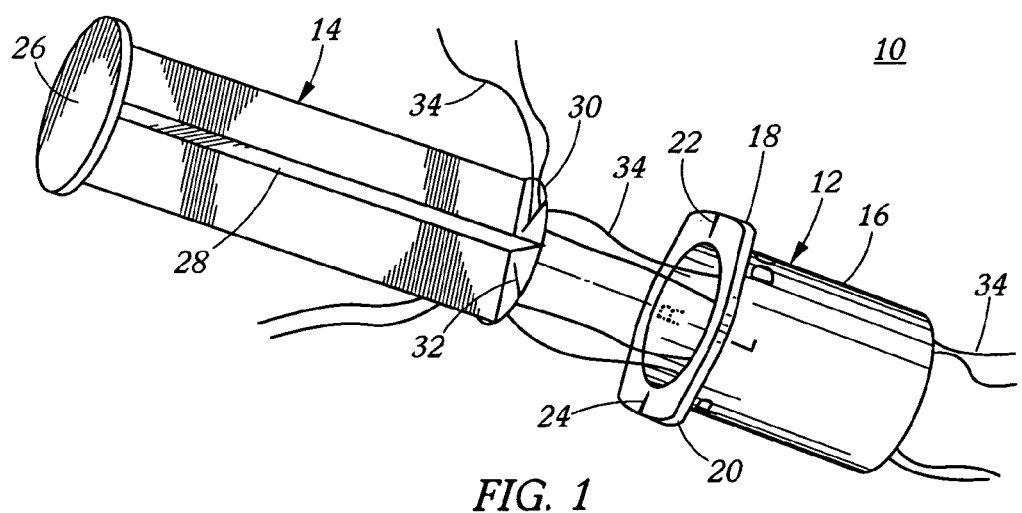
FIG. 1 is an exploded view of one embodiment of the protective device in accordance with the instant invention showing the relationship of the tubular element and the suture shuttle element as the sutures are shuttled through the tubular element.

Turning to FIG. 1, there is shown device 10 for umbilicus protection during abdominal surgery comprising a tubular element 12 and a plunger type, suture shuttle element 14. Tubular element 12 has a cylindrical housing 16 of sufficient inside diameter to house the umbilical pedicle when the tubular element 12 is tensioned in place. Tubular element 12 contains opposing ears 18 and 20, disposed upon the cylindrical housing 16 at its proximal end and containing notches 22 and 24, respectively, for releasabley frictionally engaging suture material 34 as will be later shown.

Suture shuttle element 14 has affixed to the top thereof a plunger type, circular knob 26. A set of ribbed portions 28 is connected on one end to the circular knob 26 and to an end plate 30 on the other. End plate 30 contains notches 32 spaced in each quadrant, as better shown in FIG. 3B. The ribbed portions 28 are adapted for guiding suture shuttle element 14 through the opening in tubular element 12. The ribbed portions 28 have an outside diameter of approximately the same dimension as the inside diameter of tubular element 12.

Figure 2:
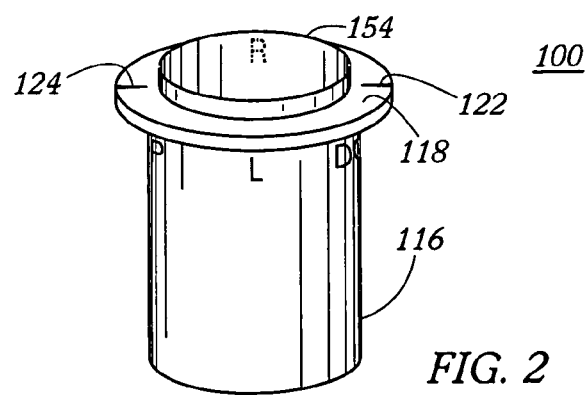
FIG. 2 is a side illustrational view of another embodiment of the tubular element in accordance with the invention.

Turning to FIG. 2, there is shown another embodiment of the tubular element 12 of FIG. 1 designated as tubular element 100. Tubular element 100 has a cylindrical housing 116 of sufficient inside diameter to house the umbilical pedicle when the tubular element 100 is in place. Tubular element 100 contains a circular lip 118, disposed upon the proximal end of cylindrical housing 116 and contains opposing notches 122 and 124, respectively. Tubular element 100 also contains an upstanding, circular collar 154 elevated from the circular lip 118 and containing notches therein, which correspond to notches 122 and 124, all such notches being adopted for releasabley frictionally engaging suture material (not shown). It will be realized by the skilled artisan that tubular element 100 can be of various configurations including differing shapes, diameters and lengths. Advantageously, tubular element 100 contains marking on the outer diameter, at the proximal end, as shown, indicating UP, DOWN, LEFT ("L"), and RIGHT ("R"). The UP and DOWN nomenclature are coincident with notches 124 and 122, respectively.

Figure 3A:
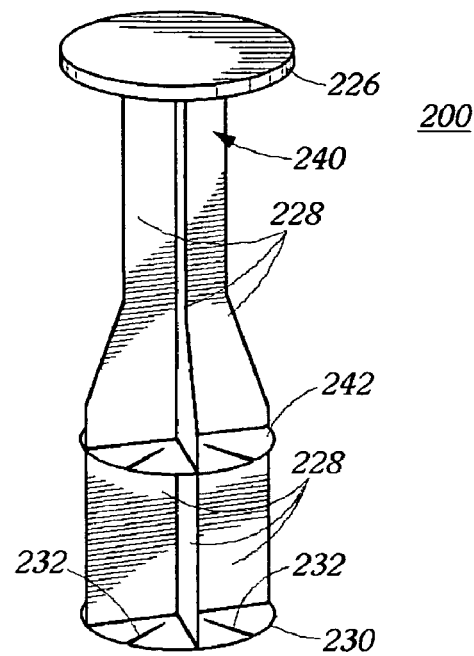
FIG. 3A is a side view of another embodiment of the plunger type, suture shuttle element in accordance with the invention.
Figure 3B:
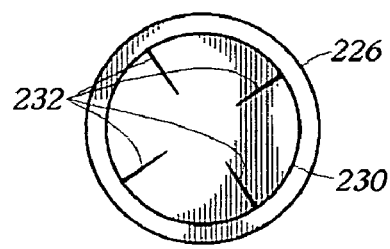
FIG. 3B is an end view of the plunger type, suture shuttle element of FIG. 3A in accordance with the invention.

Turning to FIG. 3A, there is shown another embodiment of suture shuttle element 14 designated as suture shuttle element 200. The suture shuttle element 200 has a narrowed neck portion 240, for ease of handling, and is connected on one end to the plunger type, circular knob 226 and to a circular guide plate 242 on the other. Ribbed portions 228 are narrowed at the neck 240 and extend the length of suture shuttle 200, passing through guide plate 242 and terminate at end plate 230, which carries notches 232 as better shown in FIG. 3B. FIG. 3B is an end view of suture shuttle 200 as shown in FIG. 3A. FIG. 3B shows the outline of plunger type circular knob 226 and end plate 230 with notches 232. The guide plate 242 and the end plate 230 have outside diameters approximate of the inside diameter of the tubular element to permit guided sliding of the suture shuttle element 200 within the tubular element (100 or 12).

In accordance with the invention, the tubular element can be made of any suitable material compatible with surgical procedures and advantageously latex free plastic. The tubular element is preferably sized in accordance with the surgery to be performed and physical attributes of the patient. It need not be circular. For example, lengths in the range of 6–8 cm have been found useful. Advantageously, the tubular element comes in varies sizes which are color coded for ease of use in the operating theater. For example:

| Length | Diameter |
| --- | --- |
| 40 mm (yellow) | 15 mm (yellow) |
| 60 mm (green) | 20 mm (green) |
| 80 mm (red) | 25 mm (red). |

The tubular element wall thickness is sufficient to provide stability during surgical procedure, for example, about 1.5 mm. The proximal end of the tubular element can contain opposing "ears" on the peripheral surface, which provides a mechanism for inserting the tubular element through the circum umbilical incision in order for the distal end of the tubular element to rest on the abdominal fascia. Preferably, these ears are oppositely disposed, and are small enough so that they do not interfere with palpating the tubular element through the new orifice during umbilical transportation. The ears are preferably notched such as to bisect the tubular element and provide releasable securing for the strands of suture material as previously described. It will be realized that the tubular element does not need to carry the previously described earring. In this embodiment, the notch for releasabley securing the suture material can be directly carried in the tubular element, proximate the end wall.

In accordance with one aspect, the outer proximal end of the tubular element carries, advantageously, below the notched ears, markings "UP" (12 o'clock) and "DOWN" (6 o'clock). In the other quadrants (at 3 o'clock and 9 o'clock) are respectively markings "L" and "R." In this manner, the initial placing of the tubular element, after pedicle dissection, is aligned with the mid-section of the patient (UP and DOWN), such that UP is proximate the patient's head and DOWN is proximate the patient's feet with, for example, left and right designating surgeons' left and right, or alternately, patient's left and right.

The suture shuttle element is advantageously of the same material as the tubular element, and contains a ribbed guide on its outer diameter. It is of the same lengthwise geometric shape as the tubular element. The outer diameter of the suture shuttle is of the same dimension as the inner diameter of the tubular element. The length of the suture shuttle element is advantageously greater than the tubular element, such that upon complete insertion of the suture shuttle element into the tubular element, the distal end of the suture shuttle element carrying the notches is exposed. The suture shuttle can, for example, be of three sizes according to the length and diameter of the tubular element so long as the suture shuttle element is of a length greater than that of the tubular element. The sizes are for example: 1.) 80 mm shuttle element for 40 mm tubular element; 2.) 100 mm shuttle element for 60 mm tubular element; and, 3.) 120 mm shuttle element for 80 mm tubular element.

At the distal end of each size suture shuttle are four notches for tacking suture material engaging and are advantageously located at 3, 6, 9 and 12 o'clock position. The distal end of the suture shuttle element contains a circular plate carrying the four peripheral notches for releasabley securing the strands of suture material as further described below. In one embodiment, the various tubular element diameters and lengths, as previously described, are color-coded with the corresponding suture shuttle element of the same color for use therewith. In this manner, during surgery the appropriate suture shuttle element can be instantaneously matched with the appropriate tubular element for a particular surgical scenario.

The suture material that can be used in accordance with the instant invention is preferably Ethibond® brand sutures, but only need to be of sufficient tensile strength to secure the distal end of the tubular element against the abdominal fascia through out the surgical procedure. It is used for tacking only and removed upon completion of the surgery.

Figure 4:
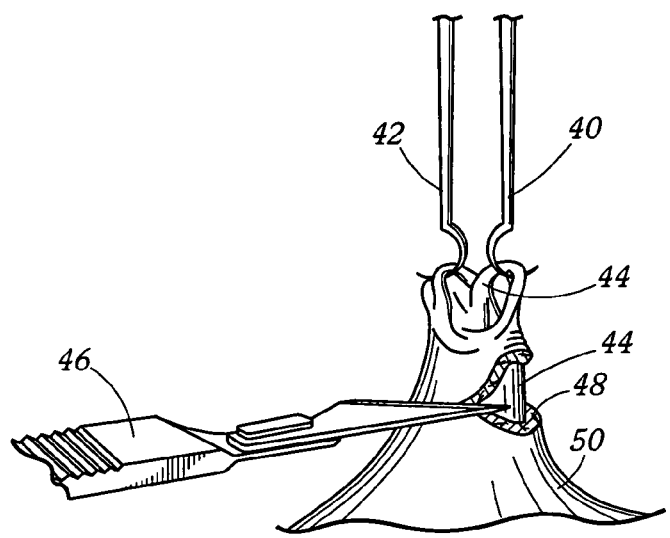
FIG. 4 is an illustration of an initial circum umbilical incision

In accordance with the method of the invention, FIGS. 4 through 13 shows the step-by-step procedure for use of the device of the instant invention during the performance of an abdominoplasty. For exemplary purposes only, the method of the instant invention will track an abdominoplasty, which begins, by circumcision of the umbilicus as shown in FIG. 4. In accordance with FIG. 4, an umbilicoplasty is shown. Skin hooks 40 and 42 lift umbilicus 44 for dissection by scalpel 46 to perform a circum peripheral umbilical dissection 48. Once the dissection takes place, skin hooks 40 and 42 are removed and the umbilicus 44 relaxes within the circum umbilical incision.

Figure 5:
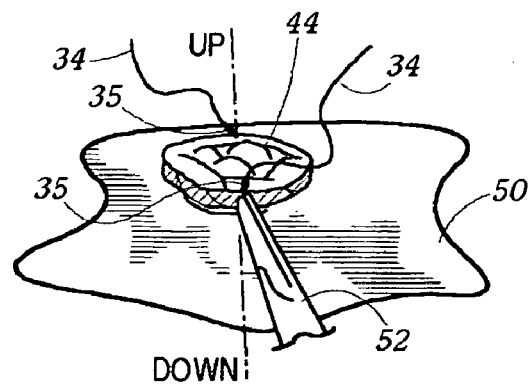
FIG. 5 is an illustration of the initially circumcised umbilical showing placement of the tacking sutures in accordance with the instant invention.
Figure 6:
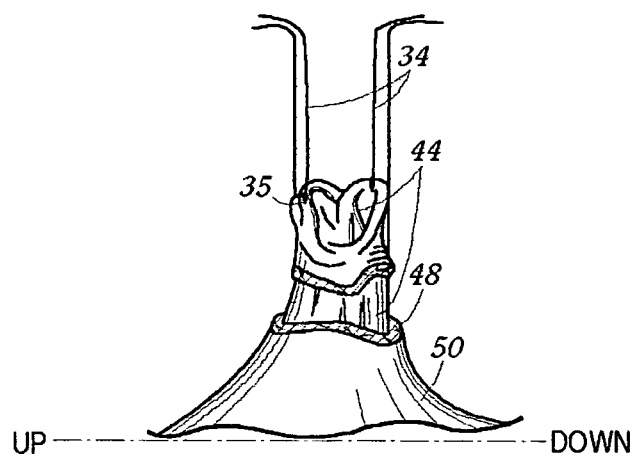
FIG. 6 is an illustration of the dissected umbilicus with tacking stitches and suture material in accordance with the invention.
Figure 7:
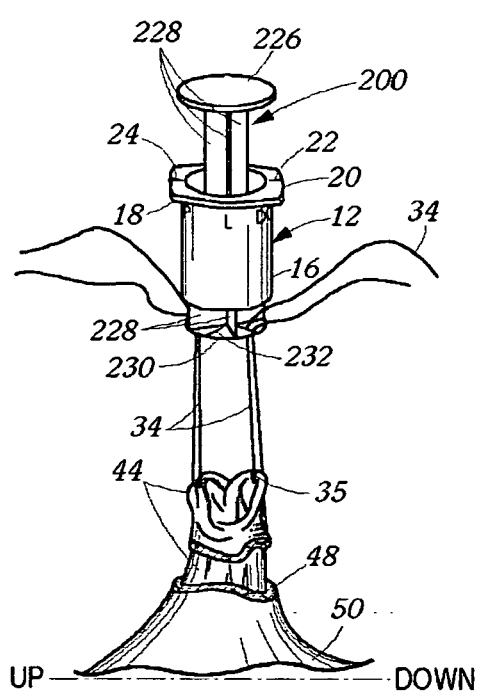
FIG. 7 is an illustration of the suture shuttle element placement in the tubular element with suture material placement in accordance with the invention.

As shown in FIG. 5, tacking sutures 35 are taken on the dissected umbilicus 44 at the superior (UP) and inferior (DOWN) positions. Sufficient suture material 34 is provided to allow tubular element 12 placement, as was described above. Turning to FIG. 6, there is shown preparation for tubular element attachment. The suture material 34, connected to the umbilicus 44 by means of tacking stitches 35, is lifted to separate the umbilicus 44 from abdominal flap 50. As shown in FIG. 7, the suture shuttle element 200 (or 14 depending on the embodiment used) is inserted into tubular element 12 such that suture shuttle element 200 protrudes beyond the distal end of cylindrical housing 16 exposing ribbed portion 228 and end plate 230 containing notches 232. The extended suture material 34 is placed within notches 232 as shown.

Figure 8:
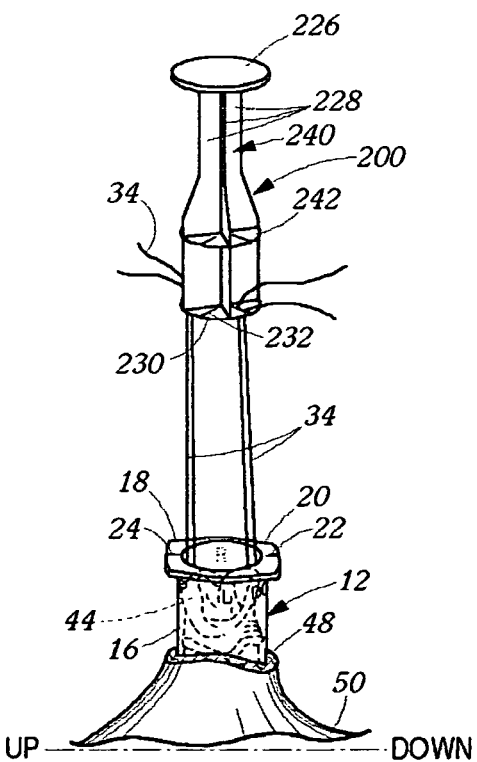
FIG. 8 is an illustration of the suture shuttle element as it is pulled out of the tubular element to seat the tubular element around the umbilicus for dissection of the umbilical pedicle in accordance with the invention.

As seen in FIG. 8, the suture shuttle element 200 is pulled, by means of the plunger type, circular knob 226, to extract the suture shuttle element 200 from the tubular element 12 thereby pulling suture material 34 attached to end plate 230 through tubular element 12. Simultaneously, tubular element 12 is pushed down by means of ears 20 and 18 into circum umbilical incision 48. Tensioning on suture material 34 moves umbilicus 44 within the interior of cylindrical housing 16, as shown in phantom. Likewise, the UP marking and the DOWN marking on tubular element 12 are aligned with the head of the patient and the feet of the patient respectively.

Figure 9:
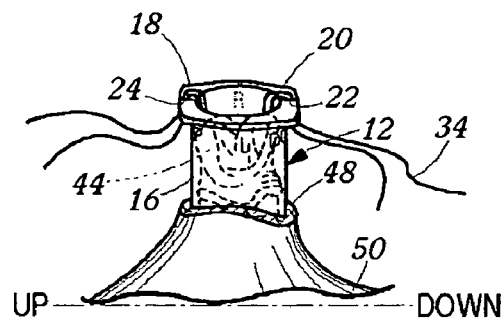
FIG. 9 is an illustration of the suture material as tensioned in the notched ears of the tubular element after umbilical pedicle dissection as placed for surgery.

As seen in FIG. 9, placement of tubular element 12 is completed by removing suture material 34 from notches 232 in end plate 230 of suture shuttle element 200 and placing the suture material 34 in notches 24 and 22 in ears 20 and 18 respectively. As can be seen, umbilicus 44 is retained within tubular element 12, and the distal end of tubular element 12 protrudes into circum umbilical incision 48 such that the complete stalk of umbilicus 44 is protected and separated from abdominal flap 50. Dissection of the umbilicus 44 is then accomplished by scalpel or scissors following the outer circumference of cylindrical housing 16 down to the abdominal fascia 56 while maintaining pressure on the ears 20 and 18 to seat the distal end of tubular element 12 on the abdominal fascia 56. Suture material 34 can then be re-tensioned in notches 22 and 24 as necessary to retain the entire stalk of umbilicus 44 down to the abdominal fascia 56 within housing 16. When the tubular element 12 is in place and houses the dissected umbilicus 44 in housing 16, by means of tensioned suture material 34 retained releasable engaging notches 22 and 24, the distal end of cylindrical housing 16 rests on abdominal fascia 56 and protrudes through abdominal flap 50 and through the subcutaneous fatty layer to protect the entirety of the stalk of umbilicus 44.

Figure 10:
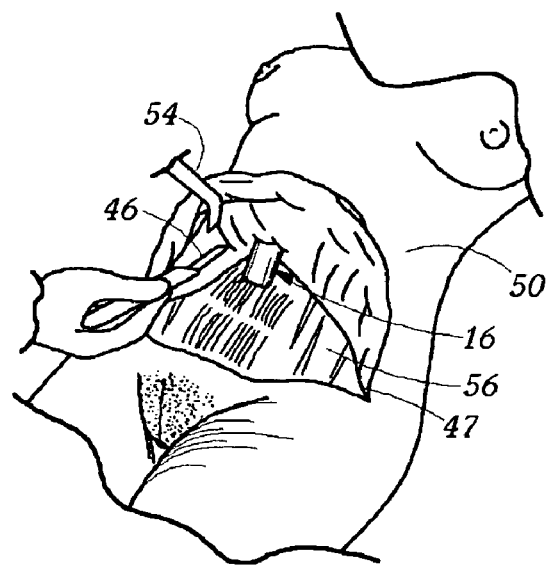
FIG. 10 is an illustration of abdominal flap dissection with the tensioned tubular element in place about the umbilical pedicle.

As shown in FIG. 10, lateral abdominal incision 47 is then made to allow abdominal flap 50 to be lifted as shown. Because the stalk of umbilicus 44 is protected via cylindrical housing 16, the stalk of umbilicus 44 is protected from nicks, cuts, and even amputation from scalpel 46. As the abdominal flap 50 is lifted and de-fattened, abdominal fascia 56 is exposed. As abdominal flap 50 is lifted past the tubular element 12 which is allowed to slip through circum umbilical incision 48 by means of movement of, for example, retractor 54.

Figure 11:
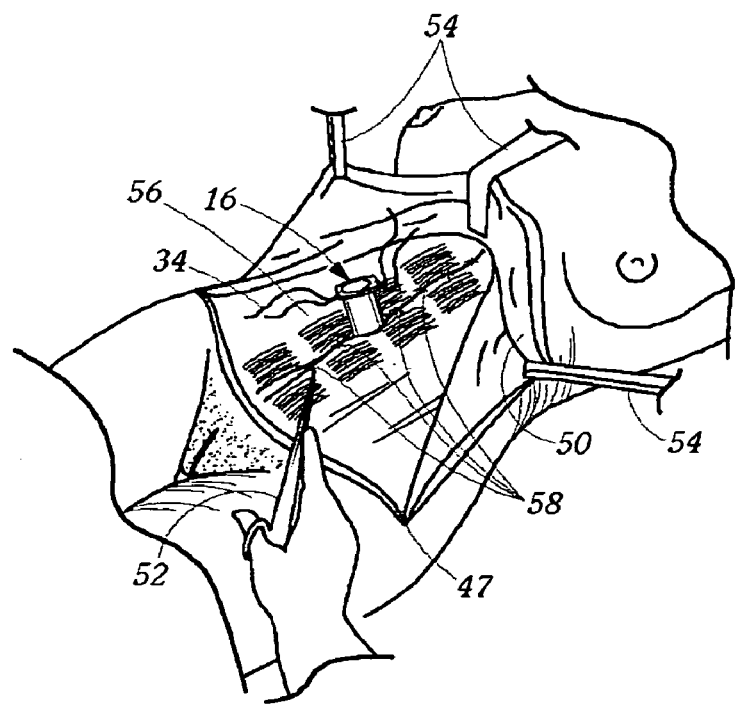
FIG. 11 is an illustration of the tubular element in place around the umbilical pedicle during rectus abdominis musculoaponeurotic plication.

As better seen in FIG. 11, with abdominal flap 50 completely lifted, de-fattened, and held by retractors 54, midline musculoaponeurotic plication sutures 58 are taken with suture forceps 52 in performing rectus abdominis musculoaponeurotic placation. Because the cylindrical housing 16 completely envelops the stalk of umbilicus 44, the tubular element 12 prevents strangulation of the umbilical pedicle by the musculoaponeurotic plication midline sutures 58.

Figure 12:
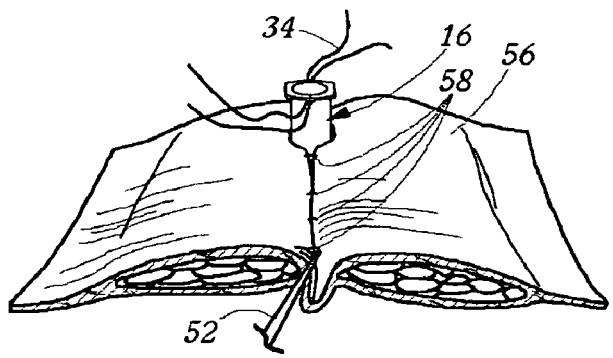
FIG. 12 is a side view of FIG. 11 showing the placement of the tubular element.

As better seen in FIG. 12, the abdominal fascia 56 bears the musculoaponeurotic plication midline sutures 58, but the sutured abdominal fascia 56 is separated from the stalk umbilicus 44 by means of cylindrical housing 16 while the superior and inferior umbilicus 44 positioning is maintained by alignment of the markings (UP, DOWN, R, and L) to prevent "twist-type" strangulation, which in the prior art procedure could not be readily detected. It will be realized by those skilled in the art that the original umbilical orifice is removed with excess abdominal skin below the lateral abdominal incision line 47 (not shown). When the abdominal flap 50 is "re-draped," the excess skin is excised at the lateral abdominal incision 47 with tension on the abdominal flap 50.

Figure 13:
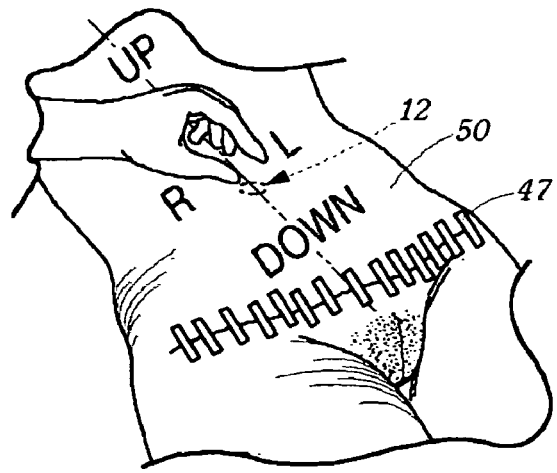
FIG. 13 is an illustration of placement of a palpated new umbilicus in accordance with the invention.

FIG. 13 shows the umbilical transposition in accordance with one aspect of the invention. The tubular element 12 helps to determine exactly the correct new umbilical orifice position, as shown in phantom in FIG. 13. The surgeon is able to feel the proximal end of tubular element 12 to indicate the exact location of the umbilicus 44, which lies beneath the abdominal flap 50. The new site of the umbilical orifice is located exactly by excavation of the tubular element 12 through the abdominal flap 50. Once the excavating incision is made, the proximal end of the tubular element 12 is exposed and protrudes through the new umbilical orifice (not shown).

In accordance with the invention, the operation of the device for umbilicus protection during abdominal surgery involves placing the entire stalk of the umbilicus within the tubular element. The tacking stitches are advantageously taken at the outer circumference of the umbilicus: one in the UP or 12:00 o'clock position and the other in the DOWN or 6:00 o'clock position. Thus, one is inserted subcutaneously in the pedicle at the point, which marks superior aspect of the midline on the umbilicus; and, the second is taken subcutaneously in the button at the point, which marks inferior aspect of the midline on the umbilicus. The suture material needs to be of sufficient length to protrude the length of the tubular element to be releasabley retained in the tubular element notches near the proximal end of the tubular element as previously described. Advantageously, the suture material should be of a length at least twice that of the length of the tubular element. The two tacking stitches, located subcutaneously in the superior and the inferior point of the midline on the umbilicus, are then secured to the suture shuttle element, which has been inserted into the cylindrical housing of the tubular element, as previously described. The distal end of the cylindrical housing of the tubular element is then placed into to the circum umbilical incision performed earlier and pushed down with the index and thumb and at the same time keeping both tacking stitches in tension. This maneuver pulls the umbilical pedicle up and pushes the tubular element down while isolating the pedicle inside the tubular element with the abdomen skin still attached.

In one embodiment, tacking stitches are taken prior to dissection, and the suture material is used to secure the umbilicus for umbilical dissection. In accordance with the embodiment where the tubular element contains the ring shaped electrocautery blade, the umbilical pedicle is dissected through the subcutaneous fat to the abdominal fascia. Once the tacking stitches are in place and the umbilical pedicle dissected, the suture shuttle element is placed into and through the tubular element, such that the distal end of the suture shuttle element protrudes the distal end of the tubular element. The suture material is then affixed to the distal end of the suture shuttle element as previously described and drawn by means of extraction of the suture shuttle element through the interior of the tubular element. In the embodiment wherein the tubular element contains the ring shaped electrocautery blade, the suture material is first drawn through the tubular element prior to umbilical pedicle dissection, energy source is attached to electrocautery circular shaped blade and energized such that pressure on the proximal end and ears of the tubular element dissects the umbilical pedicle to the abdominal fascia.

Once the distal end of the tubular element is secured against the abdominal fascia, the suture material tacked at the 12:00 o'clock position is secured under tension to the notch in the proximal end of the tubular element marked UP and the suture material tacked at the 6:00 o'clock position is secured under tension to the notch in the proximal end of the tubular element marked DOWN. It will be realized by the skilled artisan that, if necessary, a second set of tacking sutures can be secured to the left (3:00 o'clock) and right (9:00 o'clock) positions of the umbilical pedicle and secured, under tension, to corresponding notches at the corresponding positions in the proximal end of the tubular element.

The presence of the tubular element secured, as previously described, protects the umbilical pedicle from "excessive defattening" during circum umbilical pedicle dissection down to the abdominal fascia. Once the device is secure against the abdominal fascia, the lower abdominal incision and dissection of the abdominal flap is accomplished. The tubular element housing protects the stalk of the umbilical pedicle from nicking or amputation during abdominal flap undermining around the umbilical pedicle using blade or scissors.

An exemplary procedure includes a circum umbilical incision of about 3–5 mm deep. Then two, 2/0 Ethibond® tacking stitches are placed at the superior and inferior position in the umbilicus. The suture material is fastened to the distal end of the suture shuttle element, which has been inserted into the tubular element, and the suture material is withdrawn through the opening in the tubular element. As previously described, the distal end of the tubular element is then placed into to the circum umbilical incision performed earlier and pushed down with the index finger and thumb and at the same time keeping both tacking stitches in tension.

A straight down dissection of the umbilicus and its pedicle is preformed around the outer circumference of the tubular element while keeping pressure on placement of the tubular element with the index finger and thumb. The dissection is performed with scissor or electrocautery knife straight down on the outer wall of the tubular element. During this dissection, the tubular element moves down to the abdomen fascia, protects the umbilical pedicle from burn or mechanical damage, and protects from excessive "defattening." The tacked superior suture material is then fixed in a notch on the tubular element, marked UP, at the same time pushing the tubular element down. The same maneuver is accomplished with the inferior suture material fixing it in the second notch of the tubular element, marked DOWN.

The tubular element, which now protrudes through the abdominal flap and through the subcutaneous fat to the abdominal fascia, is under constant pressure downward due to the secured tacking suture material, while constantly pulling the stalk of the umbilicus up inside the tubular element. Thus, the umbilical pedicle, inside the tubular element, is completely isolated and protected. Any type of dissection can now be performed around the umbilical pedicle.

The lower abdominal incision is made and abdominal flap is elevated. Dissection of the abdominal flap using electrocautery knife around the protected umbilical pedicle is performed. The umbilical pedicle is protected and secured by the tubular element, preventing cutting of the umbilical pedicle. The abdominal flap is elevated over the tubular element leaving the tubular element secured to the abdominal fascia (wall) by means of the tacking suture material. The tubular element protects the umbilical pedicle from strangulation by sutures during musculoaponeurotic plication stage of the abdominoplasty.

When the abdominal flap is "re-draped," the excess skin, including the old umbilical orifice, is excised at the lower abdominal incision with tension on the abdominal flap. The tubular element helps to determine the correct new umbilical orifice positioning during umbilical transportation by indicating the exact location of the umbilicus, which lies under the abdominal flap. The tubular element proximal end opening corresponds with the location of the orifice on the abdomen skin. Markings are made on the abdomen skin accordingly. The new site of the umbilical orifice is located exactly by excavation of the proximal end of the tubular element.

The excess skin and fat is excised. The proximal end of tubular element (with protected umbilical pedicle inside) is exposed by applying a downward pressure on the skin proximate the new umbilicus site. The tubular element then "pops-out" through the incision in abdomen skin. During the suturing of the new umbilicus position, the sutures in notches (UP and DOWN markings on the tubular element) positioned at 12 and 6 o'clock and sides tubular element's markings R and L located on the tubular element at 9 and 3 o'clock position prevent and protect the umbilical pedicle from twisting and as a consequence from strangulation and necrosis.

All of the methods and systems disclosed and claimed herein can be made and executed without undue experimentation in light of the present disclosure. While the methods and systems of this invention have been described in terms of embodiments, it will be apparent to those of skill in the art that variations may be applied to the methods and systems and in the steps or in the sequence of steps of the methods described herein without departing from the concept, spirit, and scope of the invention. Various substitutions can be made to the hardware and software systems described without departing from the spirit of the invention. All such similar substitutes and modifications apparent to those skilled in the art are deemed to be within the spirit, scope, and concept of the invention as defined by the appended claims.

What is claimed is:

1. A method for protecting an umbilicus during subcutaneous abdominal surgery comprising circum dissecting the umbilicus and enveloping the umbilical and the umbilical pedicle within an open ended vessel, which vessel has a distal end and a proximal end, proximate the distal end to thereby protect the umbilical and the umbilical pedicle during the subcutaneous surgery.

2. The method of claim 1 wherein said vessel comprises a tubular element.

3. The method of claim 1 wherein said enveloping is accomplished by drawing said umbilical pedicle interior said vessel.

4. The method of claim 3 wherein said drawing is accomplished by means of tacking sutures in said umbilicus.

5. The method of claim 4 wherein said tacking sutures are drawn through said vessel by means of a suture shuttle element.

6. The method of claim 5 wherein said tacking sutures are maintained in tension within said vessel by means of notches on the proximal end of said tubular element.

7. A method for protecting the umbilicus during abdominal surgery comprising the steps of:
   a. circum dissecting the umbilicus;
   b. securing at least a pair of tacking sutures to the superior and inferior point of the midline of the umbilicus;
   c. inserting a suture shuttle through a tubular element;
   d. attaching the suture material from the tacking sutures to notches contained in the distal end of the suture shuttle element;
   e. pulling the suture shuttle element through the tubular element while pushing the tubular element into the circum dissected incision to capture the umbilical pedicle interior the tubular element;
   f. tensioning the suture material to draw the umbilical pedicle within the tubular element; and,
   g. attaching the suture material to the tubular element.

8. The method of claim 7 wherein the tubular element has notched opposing ears for attaching the suture material to said tubular element.

9. The method of claim 7 wherein said tubular element contains, on the proximal outer surface thereof, markings in relationship to such notches to orient the tubular element, relative to the notches.

10. The method of claim 9 wherein said superior tacking suture corresponds to an "UP" marking on said tubular element and the inferior tacking suture corresponds to a "DOWN" marking on the tubular element.

11. The method of claim 7 wherein said tubular element has notches disposed in the end wall of said tubular element for attaching said sutures.

12. The method of claim 7 comprising the further step of dissecting said umbilical pedicle by dissecting proximate the exterior of said tubular member from the abdominal skin to the to the abdominal fascia.

13. A method for protecting an umbilicus during subcutaneous abdominal surgery comprising circum dissecting the umbilicus and enveloping the umbilical and the umbilical pedicle within an open ended vessel during surgery wherein said enveloping is accomplished by drawing said umbilical pedicle interior said vessel by means of tacking sutures in said umbilicus.

14. The method of claim 13 wherein said vessel comprises a tubular element.

15. The method of claim 13 wherein said tacking sutures are drawn through said vessel by means of a suture shuttle element.

16. The method of claim 13 wherein said tacking sutures are maintained in tension within said vessel by means of notches on the proximal end of said tubular element.

* * * * *